(12) United States Patent  
Ryu et al.

(10) Patent No.: US 9,310,337 B2  
(45) Date of Patent: Apr. 12, 2016

(54) NON-DESTRUCTIVE INSPECTION DEVICE FOR PRESSURE CONTAINERS USING LEAKAGE-FLUX MEASUREMENT

(75) Inventors: Kwon Sang Ryu, Daejeon (KR); Soo Young Park, Daejeon (KR); Yun-Hee Lee, Daejeon (KR); Seung Hoon Nahm, Daejeon (KR); Un Bong Baek, Daejeon (KR)

(73) Assignee: KOREA RESEARCH INSTITUTE OF STANDARDS AND SCIENCE (KR)

( * ) Notice: Subject to any disclaimer, the term of this patent is extended or adjusted under 35 U.S.C. 154(b) by 155 days.

(21) Appl. No.: 13/977,978

(22) PCT Filed: Jan. 5, 2012

(86) PCT No.: PCT/KR2012/000110  
§ 371 (c)(1),  
(2), (4) Date: Sep. 16, 2013

(87) PCT Pub. No.: WO2012/093865  
PCT Pub. Date: Jul. 12, 2012

(65) Prior Publication Data  
US 2014/0002068 A1 Jan. 2, 2014

(30) Foreign Application Priority Data  
Jan. 6, 2011 (KR) .................. 10-2011-0001344

(51) Int. Cl.  
*G01N 29/14* (2006.01)  
*G01N 29/28* (2006.01)  
*G01N 27/82* (2006.01)

(52) U.S. Cl.  
CPC ..................................... *G01N 27/82* (2013.01)

(58) Field of Classification Search  
CPC ..... G01N 27/72; G01N 27/82; G01N 27/745; G01N 35/0098

USPC ........... 324/450, 353, 401, 460, 754.15, 331, 324/345, 463, 200, 219, 220, 221, 324/228–243; 73/623, 622, 643, 587, 592, 73/598, 597, 594, 779  
See application file for complete search history.

(56) References Cited

U.S. PATENT DOCUMENTS 3,654,504 A * 4/1972 Susdorf .................. H02K 5/148  
    310/239  
5,581,037 A * 12/1996 Kwun ..................... G01N 29/14  
    324/220

(Continued)

FOREIGN PATENT DOCUMENTS

| JP | 03127017 | 5/1991 |
| JP | 06201655 | 7/1994 |
| JP | 07198683 | 8/1995 |

(Continued)

OTHER PUBLICATIONS

International Search Report—PCT/KR2012/000110 dated Sep. 3, 2012.

*Primary Examiner* — Patrick Assouad  
*Assistant Examiner* — Taqi Nasir  
(74) *Attorney, Agent, or Firm* — Cantor Colburn LLP

(57) ABSTRACT

Provided is a non-destructive inspection device for pressure containers using leakage-flux measurement, including: a coil winding mount disposed at one side on an outside of the pressure container to magnetize the pressure container; a sensor support provided with a plurality of magnetic field sensing sensors arranged at the other side on the outside of the pressure container; a yoke magnetizing the pressure container to generate a magnetic flux in a direction vertical to a direction of the magnetic flux generated by the coil winding mount; an endoscope attached with at least one magnetic field sensing sensor, and the like.

5 Claims, 2 Drawing Sheets

(56) References Cited

U.S. PATENT DOCUMENTS

| | | | |
|---|---|---|---|
| 6,624,628 B1 * | 9/2003 | Kwun | G01N 29/11 324/240 |
| 8,049,494 B2 | 11/2011 | Lepage et al. | |
| 2008/0042645 A1 * | 2/2008 | Kaack | G01N 27/87 324/220 |
| 2008/0108870 A1 * | 5/2008 | Wiita | A61B 1/05 600/112 |
| 2009/0315129 A1 * | 12/2009 | Albertini | 257/427 |
| 2011/0037461 A1 * | 2/2011 | Braun | G01N 27/87 324/240 |

FOREIGN PATENT DOCUMENTS

| | | |
|---|---|---|
| JP | 08152424 | 6/1996 |
| JP | 10038855 | 2/1998 |
| JP | 2000074885 | 3/2000 |
| JP | 2008286798 | 11/2008 |
| WO | 2009127316 | 10/2009 |

* cited by examiner

NON-DESTRUCTIVE INSPECTION DEVICE FOR PRESSURE CONTAINERS USING LEAKAGE-FLUX MEASUREMENT

TECHNICAL FIELD

The present invention relates to a non-destructive inspection device for pressure containers using leakage-flux measurement, and more particularly, to a technology of detecting an irregular magnetic signal occurring due to a defect of a pressure container to check whether the pressure container is defective. That is, the present invention relates to a technology of more rapidly diagnosing whether a pressure container is defective by measuring a magnetic flux leaked at a cracked or defective portion of the pressure container by a magnetic sensor when a magnetic field is applied to the pressure container.

BACKGROUND ART

An example of a non-destructive method used to inspect defects may include visual inspection, ultrasonic inspection, radiation inspection, magnetic particle inspection, penetrate inspection, eddy current inspection, and the like. The visual inspection and the ultrasonic inspection rely on experience and subjectivity of an examiner, and thus has less reliability and reproducibility and the radiation inspection is difficult to inspect linear defects, such as cracks vertical to a inspection surface, and the like, and the eddy current inspection may inspect defects on a surface of a conductive material or in the vicinity of the surface.

Since a magnetic flux leakage (MFL) method for measuring a magnetic flux leaked due to defects on inner and outer walls of a subject uses a magnetic field, the MFL measuring method may be used only in a structure made of ferromagnetic materials, but may relatively easily perform an inspection, may be less affected by a size, a shape, or the like of an inspection object, and may easily identify a kind of defects.

FIG. 1 illustrates a phenomenon in which a magnetic flux is leaked at a defective site. In FIG. 1, a defect 61 generates a large magnetic resistance when a subject 60 is magnetized. In this case, a bypass magnetic flux is collected around a defect, such that the strength of an effective magnetic field may increase. A large increase in magnetic induction increases the strength of the effective magnetic field. The subject is applied with a tensile stress by an internal stress, such that the defect of the subject may serve as a stress raiser, thereby increasing permeability around a defect.

Therefore, lines of magnetic force flowing in the subject are collected at a lower portion of a defect with increased permeability as illustrated in FIG. 1. In this small region, the lines of magnetic force are behaved like a magnetic line dipole. The dipole has the same direction as the magnetic field disturbed in the subject and generates the magnetic field having an opposite direction to the leakage flux in the defect. Therefore, a defect may be detected by measuring the leakage flux even at a portion at which the defect is present or an opposite portion thereto.

Various types of equipments of detecting the leakage flux as described above have been proposed, but an example thereof may include a yoke type inspection equipment as illustrated in FIG. 2. The inspection device is configured to include a yoke 30 which magnetizes the subject 60, a power supplier which applies a current to a coil wound around the yoke 30, a magnetic field sensing sensor 50, an analyzer which analyzes an output signal from the magnetic field sensing sensor, and the like.

The related art has used an ultrasonic inspection method to sort out inferior goods during a manufacturing process of a vessel. The ultrasonic inspection method is difficult to perform an accurate measurement when a inspection device does not firmly contact a surface of the vessel, such that it may not accurately inspect a curved portion of a dome having the highest possible occurrence of defect; however, the present invention use a non-contact method. The non-contact method may inspect the curved portion and accurately check whether a defect is present in the vessel, independent of the size of the vessel.

DISCLOSURE

Technical Problem

An object of the present invention is directed to check whether a pressure container is defective by detecting an irregular magnetic signal occurring due to the defect of the pressure container. That is, the present invention relates to a technology of more rapidly diagnosing whether a pressure container is defective by measuring a magnetic flux leaked at a cracked or defective portion of the pressure container by a magnetic sensor when a magnetic field is applied to the pressure container.

Technical Solution

In one general aspect, there is provided a non-destructive inspection device for pressure containers using leakage-flux measurement, including: a coil winding mount disposed at one side on an outside of the pressure container to magnetize the pressure container; and a sensor support provided with a plurality of magnetic field sensing sensors arranged at the other side on the outside of the pressure container.

A magnetic flux generated by the coil winding mount may penetrate through the pressure container and the defect on the outer surface of the pressure container located in a direction vertical to a direction of a magnetic flux penetrating through the pressure container may change a magnetic signal detected by the magnetic field sensing sensor.

The non-destructive inspection device for pressure containers using leakage-flux measurement may further include: a yoke magnetizing the pressure container to generate a magnetic flux in a direction vertical to a direction of the magnetic flux generated by the coil winding mount.

The magnetic field sensing sensor may be disposed under the yoke and the defect on the outer defect of the pressure container located in a direction vertical to a direction of a magnetic flux generated by the yoke may change a magnetic signal detected by the magnetic field sensing sensor.

Both ends of the yoke may be provided with steel brushes.

An endoscope attached with at least one magnetic field sensing sensor may be inserted into the pressure container to measure the defect on the inner surface of the pressure container.

The magnetic field sensing sensor may include a search coil sensor, a flux gate sensor, a hall effect sensor, a GMR sensor, an AMR sensor, a TMR sensor, and a PHR sensor.

Advantageous Effects

According to the non-destructive inspection device for the pressure containers using leakage-flux measurement according to the embodiments of the present invention, it is possible to change the magnetization direction so as to increase the defect detection capability depending on the direction of the defect. In the case of the external defect, it is possible to complete the defect measurement during the one rotation of the pressure container.

BEST MODE

Hereinafter, exemplary embodiments of the present invention will be described in detail with reference to the accompanying drawings.

Figure 1:
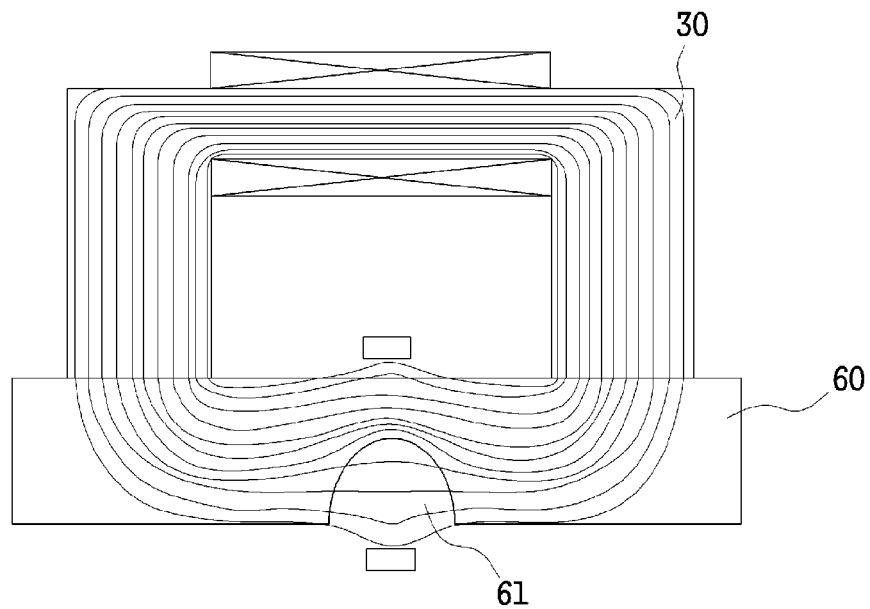
FIG. 1 is a diagram illustrating an appearance of a leakage flux occurring at a defect site of a magnetized subject.
Figure 2:
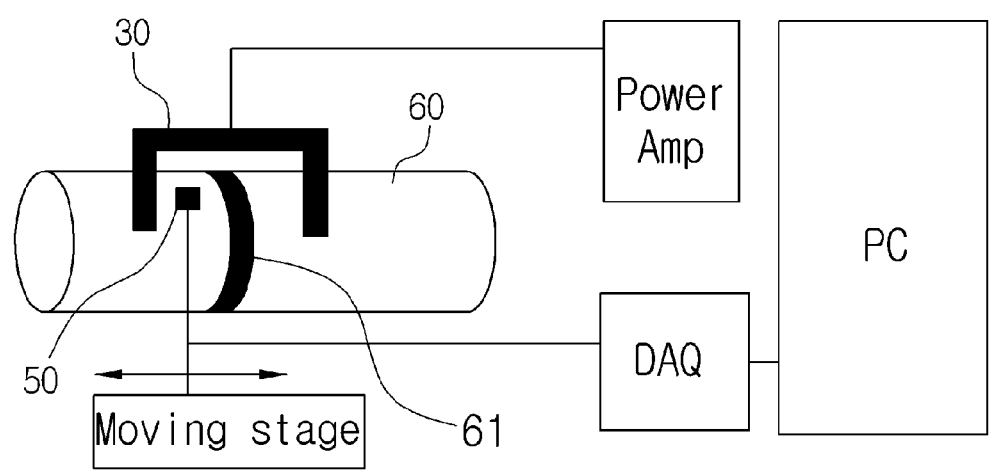
FIG. 2 is a diagram illustrating a non-destructive inspection device using leakage-flux measurement according to the related art.
Figure 3:
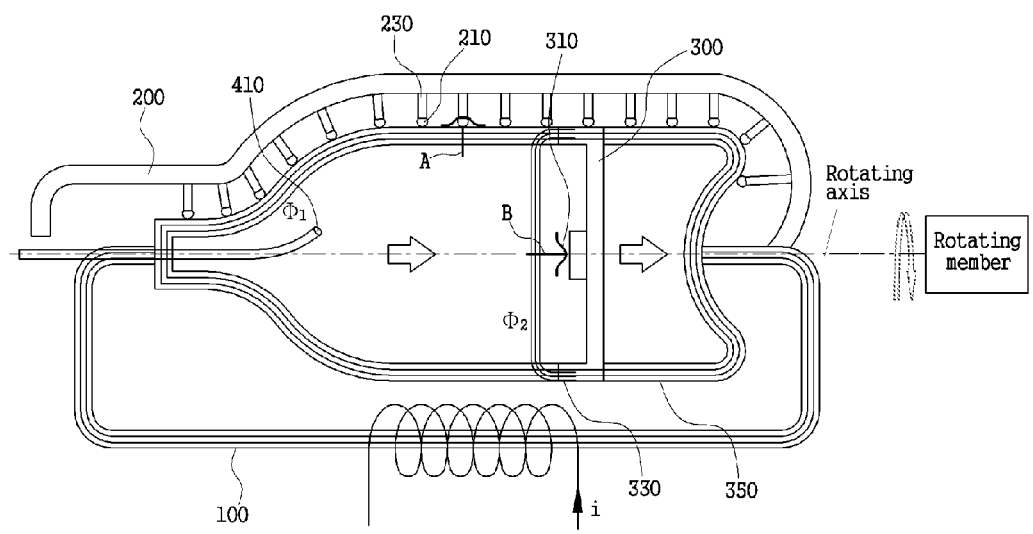
FIG. 3 is a diagram illustrating a non-destructive inspection device for pressure containers using leakage-flux measurement according to an exemplary embodiment of the present invention.

FIG. 3 is a diagram illustrating a configuration of a non-destructive inspection device for pressure containers using leakage-flux measurement according to an exemplary embodiment of the present invention.

As illustrated in FIG. 3, the non-destructive inspection device for pressure containers using leakage-flux measurement according to the exemplary embodiment of the present invention includes a coil winding mount 100, a sensor support 200, a yoke 300, and an endoscope 400.

The non-destructive inspection device for pressure containers using leakage-flux measurement according to the exemplary embodiment of the present invention measures defects on outer and inner surfaces of a pressure container 500.

The coil winding mount 100 according to the exemplary embodiment of the present invention is disposed at one portion of the outside of the pressure container 500 to magnetize the pressure container 500.

The sensor support 200 according to the exemplary embodiment of the present invention is provided with a plurality of magnetic field sensing sensors 210 which are arranged at the other side on the outside of the pressure container 500. The sensor support 200 is provided with sensor holders 230 for fixing the magnetic field sensing sensor 210.

As illustrated in FIG. 3, a magnetic flux $\phi_1$ generated by the coil winding mount 100 according to the exemplary embodiment of the present invention penetrates through the pressure container 500. A defect A on an outer surface of the pressure container 500 located in a direction vertical to a direction of the magnetic flux $\phi_1$ penetrating through the pressure container 500 changes a magnetic signal detected by the magnetic field sensing sensor 210.

Therefore, it is possible to complete the detection of the defect A on the outer surface of the pressure container 500 during the one rotation of the pressure container 500. The pressure container 500 may be provided with a handle or a motor, a belt, and the like, as members for rotating the pressure container 500. The pressure container 500 is provided with a rotation shaft. This may be implemented by various methods by a person having an ordinary skill in the art to which the present invention pertains. Further, it is possible to control a detection speed of the defect on the surface of the pressure container by controlling a rotation speed of the pressure container 500.

As described above, according to the exemplary embodiment of the present invention, the process of detecting the defect on the surface of the pressure container 500 is repeated by rotating the pressure container 500. That is, the pressure container 500 rotates by rotating the rotation shaft of the pressure container 500. As a result, the detection of the defect A on the outer surface of the pressure container 500 may be completed during the one rotation of the pressure container 500.

Further, even for the measurement of the defect on the inner surface of the pressure container 500, the defect on the inner surface of the pressure container 500 can be measured more rapidly and precisely by moving the position of the endoscope 400 at one pitch interval every rotation of the pressure container 500, like a pitch movement of a screw.

When the pressure container 500 which is an object to be inspected is magnetized by the coil winding mount 100, the leakage flux occurs at the defect A site of the pressure container 500 and the magnetic field sensing sensor 210 senses the leakage flux to detect the detect site.

The magnetic field sensing sensor 210 measures, for example, a voltage modified due to the leakage flux and may detect the presence and absence of the defect of the pressure container 500 and the defect site depending on a level of the voltage.

As illustrated in FIG. 3, the yoke 300 according to the exemplary embodiment of the present invention magnetizes the pressure container 500 to generate a second magnetic flux $\phi_2$ in a direction vertical to the direction of the magnetic flux $\phi_1$ generated by the coil winding mount 100. This is to detect the defect located in a direction which may not easily detected with the magnetic flux $\phi_1$ generated by the coil winding mount 100.

The yoke 300 does not contact the pressure container 500. The yoke 300 may include a coil wound around the outside thereof to generate a magnetic field at the yoke 300 and a power supplier supplying power to the coil.

When the magnetic flux $\phi_2$ is generated at the yoke 300 by the magnetic field generated by the power supplier and is applied to the pressure container 500, the pressure container 500 generates mutual induction to generate the magnetic flux $\phi_2$ and when a defect B is present in the pressure container 500, an impedance of the pressure container 500 is changed, and thus a magnitude of the magnetic flux $\phi_2$ is changed around the defect B.

The magnitude of the magnetic flux $\phi_2$ is also changed depending on the size of the defect B. When the change in the magnitude of the magnetic flux $\phi_2$ and the changed position thereof are detected by the magnetic field sensing sensor 310 to generate a measurement signal, an amplification circuit filters and amplifies the measurement signal and a signal processor processes the amplified measurement signal to calculate the position and size of the defect B, thereby detecting the presence and absence of the defect of the inside of the pressure container 500 and the position and size of the defect thereof.

As described above, the magnetic field sensing sensor 310 is disposed under the yoke 300 according to the exemplary embodiment of the present invention. The defect B on the outer surface of the pressure container 500 located in a direction vertical to a direction of the magnetic flux $\phi_2$ generated by the yoke 300 changes the magnetic signal detected by the magnetic field sensing sensor 310.

Both ends of the yoke 300 according to the exemplary embodiment of the present invention may be provided with steel brushes 330. The yoke 300 may be made of materials having high permeability, such as ferrite, electrical sheet, and the like. The yoke 300 may have a horseshoe shape.

Therefore, it is possible to complete the detection of the defect A on the outer surface of the pressure container 500 by advancing the yoke 300 pitch by pitch, simultaneously with the rotation of the pressure container 500.

The endoscope 400 according to the exemplary embodiment of the present invention is to measure the defect on the inner surface of the pressure container 500 and the endoscope 400 attached with at least one magnetic field sensing sensor 410 is inserted into the pressure container 500. Except for the process of using the endoscope 400, the process of measuring the defect on the inner surface of the pressure container 500 is the same as the foregoing process.

The foregoing magnetic sensing sensors 210, 310, and 410 may be implemented as a search coil sensor, a flux gate sensor, a hall effect sensor, a GMR sensor, an AMR sensor, a TMR sensor, a PHR sensor, and the like.

The non-destructive inspection device may include a circuit for amplifying and filtering the measurement signal generated by the magnetic field sensing sensors 210, 310, and 410 and a signal processor processing the amplified and filtered measurement signal to calculate the position and size of the defect of the inside of the pressure container 500.

The signal processor may further include a differential processor which differentiates the amplified and filtered measurement signal to calculate the position and size of the defect. The position and size of the defect may be more accurately calculated by the differential processing.

As described above, according to the exemplary embodiment of the present invention, the magnetization direction may be changed to increase the defect detection capability depending on the direction of the defect. In the case of the external defect, it is possible to complete the defect measurement during the one rotation of the pressure container.

The major features of the exemplary embodiment of the present invention detect the defects on the surface of the pressure container by rotating the pressure container to more rapidly complete the detection operation and change the magnetization direction by using the fact that the defects on the surface of the pressure container are detected well by the magnetic field sensing sensor when the defect is located in a direction vertical to the direction of the magnetic flux as described above. That is, the coil winding mount and the yoke are used to change the magnetization direction.

Although the present invention has been described with reference to the exemplary embodiments and the accompanying drawings, it is not limited to the above-mentioned exemplary embodiments but may be variously modified and changed from the above description by those skilled in the art to which the present invention pertains. Therefore, the scope and spirit of the present invention should be understood only by the following claims, and all of the equivalences and equivalent modifications to the claims are intended to fall within the scope and spirit of the present invention.

The invention claimed is:

1. A non-destructive inspection device for detecting defects of a pressure container using magnetic flux leakage, the non-destructive inspection device comprising:
   a pressure container configured to rotate about a rotating axis;
   a coil winding mount disposed outside of the pressure container to magnetize the pressure container and generate a first magnetic flux, the coil winding mount being disposed at one side of the pressure container with respect to the rotating axis;
   a sensor support disposed outside of the pressure container, the sensor support being disposed at the other side of the pressure container with respect to the rotating axis, the sensor support having a plurality of first magnetic field sensing sensors arranged along the rotating axis;
   a yoke magnetizing the pressure container to generate a second magnetic flux in a direction vertical to the first magnetic flux, the yoke being disposed in a direction vertical to the rotating axis, having a second magnetic field sensing sensor and configured to move along the rotating axis; and
   an endoscope attached with a magnetic field sensing sensor is inserted into the pressure container to measure the defect located on the inner surface of the pressure container,
   wherein, while the pressure container rotates, at least one of the first magnetic field sensing sensors measures magnetic flux leakage caused by a first defect present in the pressure container thereby detecting the defect,
   the endoscope moves at one pitch interval to measure the defect located on the inner surface of the pressure container, and
   the yoke moves at one pitch interval to detect a defect on an outer surface of the pressure container.

2. The non-destructive inspection device of claim 1, wherein the first magnetic flux penetrates through the pressure container; and wherein the first defect in an outer surface portion of the pressure container and located in a direction vertical to the first magnetic flux changes a magnetic signal detected by the at least one first magnetic field sensing sensor.

3. The non-destructive inspection device of claim 1, wherein the second magnetic field sensing sensor is disposed under the yoke; and wherein a second defect in an outer surface portion of the pressure container and located in a direction vertical to the second magnetic flux changes a magnetic signal detected by the second magnetic field sensing sensor.

4. The non-destructive inspection device of claim 1, wherein both ends of the yoke are provided with steel brushes.

5. The non-destructive inspection device of claim 1, wherein the magnetic field sensing sensor includes a search coil sensor, a flux gate sensor, a hall effect sensor, a GMR sensor, an AMR sensor, a TMR sensor, or a PHR sensor.

* * * * *